United States Patent [19]
McCarthy et al.

[11] Patent Number: 5,112,852
[45] Date of Patent: May 12, 1992

[54] ALLENYL AMINES

[75] Inventors: James R. McCarthy, West Chester, Ohio; Thomas M. Bargar, Clayton, Calif.; Charlotte L. Barney, Cincinnati; Donald P. Matthews, West Chester, both of Ohio; Robert J. Broersma, Noblesville, Ind.

[73] Assignee: Merrell Dow Pharmaceuticals Inc., Cincinnati, Ohio

[21] Appl. No.: 341,518

[22] Filed: Apr. 21, 1989

Related U.S. Application Data

[60] Division of Ser. No. 153,106, Feb. 8, 1988, Pat. No. 4,847,288, which is a continuation-in-part of Ser. No. 945,460, Dec. 23, 1986, abandoned.

[51] Int. Cl.$^5$ .................. A61K 31/38; C07D 333/52
[52] U.S. Cl. .................... 514/443; 549/49; 549/51; 549/52; 549/53; 549/54; 549/55; 549/56; 549/58
[58] Field of Search .............. 549/49, 51, 52, 53, 549/54, 55, 56, 58; 514/443

[56] References Cited

U.S. PATENT DOCUMENTS

| | | | |
|---|---|---|---|
| 3,598,839 | 8/1971 | Kaltenbronn | 549/49 X |
| 3,697,513 | 10/1972 | Siegnist | 549/49 X |
| 3,910,955 | 10/1975 | Chapman et al. | 549/49 |
| 4,703,058 | 10/1987 | Bargar et al. | 514/471 |
| 4,788,301 | 11/1988 | Bargar et al. | 514/438 |

OTHER PUBLICATIONS

Claesson, A., and Sahlberg, C., *Tetrahedron*. 38(3), 363-8 (1982).
Sahlberg, C., Svante, B. R. Fagewall, I., Ask, A., and Claesson, A., *J. Med. Chem.* 26(7), 1036-42 (1983).

*Primary Examiner*—Catherine S. Kilby Scalzo
*Attorney, Agent, or Firm*—William J. Stein

[57] ABSTRACT

The present invention relates to allenyl amines, more specifically, β-ethenylidene(substituted) ethanamines, possessing antihypertensive activity, and having the general formula

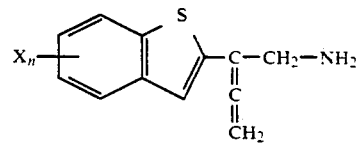

wherein n is the integer 0, 1 or 2; each X independently is a substituent selected from the group consisting of loweralkyl, halo, —O—(loweralkyl), —S—(loweralkyl), —SO—(loweralkyl), —SO$_2$—(loweralkyl), CO$_2$R and CH$_2$OR, wherein R is loweralkyl and each loweralkyl group is from 1 to about 6 carbon atoms, or the pharmaceutically-acceptable addition salts thereof. These compounds are prepared by a novel reaction of a protected N,N-bis(trimethylsilyl)-4-methoxy-2-butynylamine compound with a metallo-organic compound, with subsequent removal of the silyl protecting groups to provide the desired compound.

11 Claims, No Drawings

ALLENYL AMINES

CROSS-REFERENCE TO RELATED APPLICATION

This is a division of application Ser. No. 153,106 filed Feb. 8, 1988, now U.S. Pat. No. 4,847,288, which is a continuation-in-part of application Ser. No. 945,460, filed Dec. 23, 1986, now abandoned.

This invention relates to novel allenyl amines, the process an intermediates useful for their preparation, and to pharmaceutical compositions and methods of treating hypertension with such compositions.

More specifically, this invention relates to allenyl amines of the general formula

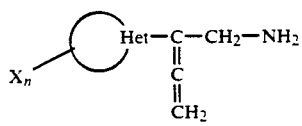

(I)

wherein Het is a furanyl, pyridinyl, thiazolyl, imidazolyl, pyrazolyl, benzthiophenyl or a thiophenyl moiety; n is the integer 0, 1 or 2; each X independently can be a substituent selected from the group consisting of loweralkyl,—O—(loweralkyl), —S—(loweralkyl), halo, wherein halo is chloro, bromo or fluoro, and $CO_2R$ and $CH_2OR$, wherein R is H or loweralkyl, and the therapeutically-acceptable acid addition salts thereof.

The Het moieties, which can optionally be substituted with 1 or 2 substituents as defined by X, are illustrated as follows:

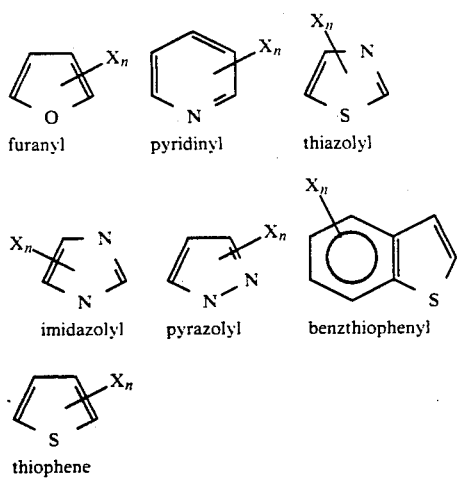

wherein n and X are above defined.

Where n is 2, the X substituents on each Het group can be the same or different, although they preferably are the same. Preferably, n is 0 or 1. R is preferably H. The term "loweralkyl" in each occurrence means from one to about 6 carbon atoms, and includes methyl, ethyl, propyl, butyl, pentyl and octyl groups, which can be straight- or branched-chain. Preferably, lower alkyl groups of from 1 to 4 carbon atoms are employed.

The following represent preferred embodiments of the compounds of the present invention:
(1) n is 0 or 1;
(2) n is 1;
n is 0;

(4) n is 1 and X is selected from the group consisting of halo and loweralkyl;
(5) the embodiment of (4) wherein Het is thiophenyl or benzthiophenyl
(6) the embodiment of (2) wherein X is —O— or —S—(loweralkyl);
(7) the embodiment of (2) wherein X is $CO_2R$;
(8) the embodiment of (2) wherein X is $CH_2OR$;
(9) the embodiment of (1) wherein Het is thiophenyl;
(10) the embodiment of (2) wherein X is loweralkyl or from 1 to 4 carbon atoms, and
(11) the embodiment of (1) wherein Het is benzthiophenyl.

Illustrative examples of the compounds of this invention include:
β-ethenylidene-2-thiopheneethanamine;
β-ethenylidene-2-furanethanamine;
β-ethenylidene benzo [b]-thiophene-2-ethanamine;
β-ethenylidene-2-pyridineethanamine;
β-ethenylidene-2-thiazoleneethanamine;
β-ethenylidene-2-imidazoleneethanamine;
β-ethenylidene-3-pyrazoleneethanamine;
β-ethenylidene-2-(5-chlorothiophene)ethanamine;
β-ethenylidene-2-(5-methoxythiophene)ethanamine;
β-ethenylidene-2-(5-carboxythiophene)ethanamine;
β-ethenylidene-2-(5-methylsulfinylthiophene)ethanamine;
β-ethenyldiene-2-(5-methylfuran)ethanamine;
β-ethenylidene-3-bromobenzo[b]-thiophene-2-ethanamine;
β-ethenyldiene-5-bromobenzo[b]-thiophene-2-ethanamine;
β-ethenyldiene-3,5-dibromobenzo[b]-thiophene-2-ethanamine;
β-ethenyldiene-2-(5-chloropyridine)ethanamine;
β-ethenyldiene-2-(5-methylthiazolo)ethanamine;
β-ethenyldiene-2-(5-methoxyimidazolo)ethanamine; and
β-ethenyldiene-2-(5-chloropyrazolo)ethanamine
and the therapeutically acceptable acid addition salts thereof.

Representative salts are those salts formed with nontoxic organic or inorganic acids, such as, for example, those formed from the following acids: hydrochloric, hydrobromic, sulfonic, sulfuric, phosphoric, nitric, maleic, fumaric, benzoic, ascorbic, succinic, methanesulfonic, acetic, propionic, tartiaric, citric, lactic, malic, mandelic, cinnamic, palmitic, itaconic and benzenesulfonic.

The allenyl amines (I) of this invention can readily be prepared by a series of reactions illustrated by the following reaction scheme:

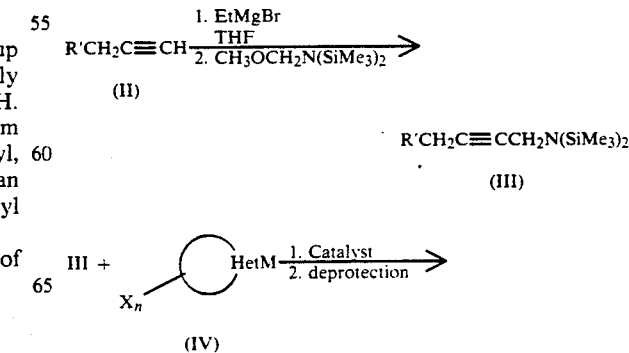

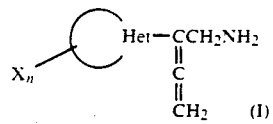

$$\text{(I)}$$

In essence, the following reaction scheme shows that the allenyl amines (I) of this invention are prepared by the novel reaction of a protected amine, N,N-bis-(trimethylsilyl)-4-alkoxy-2-butynylamine (III), with a metalloorganic compound of formula IV wherein Het, X and n are as defined above and M is an organometallo reagent, such as for example, MgBr, trimethyltin or tri-n-butyltin. In formula III, R' is an alkoxy group of 1–4 carbon atoms, and is preferably a methoxy group. The reaction is carried in an inert solvent, such as diethylether, at room temperature in the presence of a nickel catalyst, such as 1,3-bis(diphenylphosphinopropane)-nickel(II)-chloride [henceforth $NiCl_2$(dppp)], to yield silyl-protected amines. The reaction is then treated with a deprotecting agent, such as, for example, ammonium hydroxide and silica gel (column chromatography), or ethanolic hydrochloric acid or sodium fluoride, to remove the silyl protecting groups and give the desired product (I). The free bases can be converted to acid addition salts, or the acid addition salts can be converted to the free bases by conventional chemical methodology.

The trimethyl starting material (III) is prepared by the addition of ethylmagnesium bromide to a mixture of alkylpropargyl ether (II), wherein R' is an alkoxy group of 1–4 carbon atoms, and tetrahydrofuran (THF), after which N,N-bis(trimethylsilyl) methoxymethylamine is added. After dilution with ether, filtration through celite and washing with sodium hydroxide, Kugelrohr distillation yields bis(trimethylsilyl) protected 4-alkoxy-2-butynylamine (II).

When the metallo-organic starting compound in the above reaction is a Grignard reagent, it is obtained by converting the appropriate brominated heterocycle (see Het above), for example, 2-bromothiophene, by reactions with magnesium and subsequent dehydration according to standard Grignard conditions to yield, for example, 2-thienomagnesium bromide; or by converting the appropriate lithiated heterocycle, for example 2-benzothiophenyl lithium, with magnesium bromide to yield the appropriate heterocyclic magnesium bromide compound, for example, 2-benzothiophenylmagnesium bromide, after subsequent dehydration according to standard Grignard conditions.

When M in the above reaction is a tin derivative, it can be obtained in a manner consistent with the procedure of T. Bailey, *Tetrahedron Letters*, 27, 37, 4407 (1986).

The foregoing reaction scheme is further illustrated by the following specific exemplifications.

EXAMPLE 1

N,N-bis(trimethylsilyl)-4-methoxy-2-butynylamine (III)

Methylpropargyl ether (36.4 g, 0.52M) and dry tetrahydrofuran (300 ml) were added to a dry 100 ml 3-necked flask with mechanical stirrer, thermometer, and addition funnel with a nitrogen bubbler. The solution was cooled in an ice bath and ethylmagnesium bromide (262 ml, 0.52M) was added dropwise with stirring. The reaction was stirred at room temperature for 10 minutes and N,N-bis(trimethylsilyl)methoxymethylamine was added. The reaction was heated at reflux for 16 hours until complete by G C Analysis. The thick slurry was diluted with ether, filtered through a celite pad and the filtrate washed with 1 liter 30% NaOH. The product was dried over $K_2CO_3/Na_2SO_4$ and concentrated into an oil. Kugelrohr distillation at 80° C. (2 mm) gave 91 g. (77%) of III.

EXAMPLE 2

β-Ethenylidene-2-thiopheneethanamine $NiCl_2$ (dppp) catalyst (170 mg; 3M %) was added to dry ether (30 ml) in a 100 ml 3-necked flask with mechanical stirrer, thermometer and nitrogen bubbler. III (2.47 g, 10.2 mM) was added via syringe with stirring and immediately thereafter 3M thienylmagnesium bromide (7 ml, 21 mM) was added via syringe. After stirring at room temperature for 20 hours the reaction was complete as shown by G C analysis. The silylated product was isolated by shaking with dilute $NH_4OH$ and extraction into ethylacetate (three times, each into 100 ml). After drying over $K_2CO_3$ and concentration, 2.68 g crude product was obtained. Purification and desilylation by flash chromatography (300 g silica gel, eluted with $CHCl_3$, then $CHCl_3$:MeOH:conc. $NH_4OH$ 100:10:1) gave 1.22 g (87%) of the desired product as a light tan oil after drying under high vacuum.

Treatment of an etheral solution of the free base with one equivalent of 1M ethanolic p-toluenesulfonic acid or with one equivalent of an ethanolic solution of oxalic acid gave the tosylate and oxylate salts respectively. The tosylate salt was a 76% conversion from the free base, Mp 126°–127° C. (isopropanol). The oxalate salt was 72% conversion from the free base, Mp 188°–190° C. (isopropanol).

Anal Calc'd for $C_8H_9NS$: C, 55.71; H, 5.30; N, 5.30. Found: C, 55.75; H, 5.44; N, 4.28.

In like manner, by substituting optionally substituted thiazolemagnesium bromide (produced by reacting optionally substituted 2-bromo-thiazole with magnesium according to standard procedures) for thienylmagnesium and following the above procedure, the following compound, as one example of the possible compounds that can be produced, results: β-ethenylidene-2-thiazoleneethanamine.

EXAMPLE 3

β-Ethenylidenebenzo[b]thiophene-2-ethanamine

2-Benzothiophenylmagnesium bromide was prepared by adding butyllithium (5.1 ml, 15.8 mM) to benzothiophene (1.7 g, 12.7 mM) in a 3-necked, 100 ml flask with septum, stir bar, thermometer, and nitrogen inlet, in the presence of ether (15 ml), allowing reaction to reflux about 15 minutes, and then cooling to 0° C. in ice. Magnesium bromide etherate (12.7 mM) was added all at once and was allowed to warm to 20° C. over about 15 minutes. Then $NiCl_2$ (dppp) (30 mg) was added and, following the procedure described in Example 2, III (12.7 mM) was added and stirred overnight to produce the crude silylate product, the reaction being complete by G C analysis after that time. 1M ethanolic hydrochloride (0.9 equivalent), was added to the etheral solution to yield 1.7 g (72%) of hydrochloride salt as a pale yellow solid, Mp 235° C. (dec) (EtOH).

Anal. Calc'd for $C_{12}H_{11}NS \cdot HCL$: C, 60.63; H, 5.09; N, 5.89. Found: C, 60,86; H, 5.21; N, 5.65.

In like manner, by substituting optionally substituted imidazole or pyrazole (each with an appropriate protecting group at the 1 position), optionally substituted 2-, 3- or 4-bromopyridine, or optionally substituted furan for benzothiophene and following the above procedure, the following compounds, as representative examples of the possible compounds that can be produced, result respectively:

β-ethenylidene-2-imidazoleneethanamine,
β-ethenylidene-3-pyrazoleneethanamine,
β-ethenylidene-2-pyridineethanamine and
β-ethenylidene-2-furanethanamine.

Dopamine-β-hydroxylase (DBH) facilitates the conversion of dopamine to norepinephrine. Inhibition of the enzyme (DBH) causes a decrease in the amount of norepinephrine produced which in turn effectuates a lowering of blood pressure. The allenylamines of this invention (I) are dopamine-β-hydroxylase (DBH) inhibitors of a mechanism-based nature, inactivation of the enzyme being time dependent. The enzyme is inactivated directly, i.e., at the active site of the enzyme. Thus the compounds of formula I are useful as therapeutic agents in the treatment of hypertension. An embodiment of this invention thus comprises a method of treating hypertension in a mammal which comprises administering internally to said mammal an effective antihypertensive amount of compound of formula I.

The DBH inhibitory properties of the compounds of this invention can readily be determined by standard and well known procedures such as those procedures set forth in U.S. Pat. No. 4,415,591. Determination of whether the DBH inhibition demonstrates time-dependent kinetics is exemplified by a procedure wherein enzymatic oxygenation by DBH is determined in aqueous solution in the presence of molecular oxygen, an electron donor such as ascorbate, and the necessary cofactors for the enzyme at a pH of 4.5 to 5.5, preferably pH 5.0, and at a temperature of 20° C. to 40° C., preferably 37° C. The test compound is added at the desired concentration, and the system is incubated. At different time intervals aliquots are taken and DBH activity is measured using tyramine as the substrate. The reaction is followed by measuring oxygen uptake using a polarographic electrode and an oxygen monitor by the method of S. May, et al., *J. Biol. Chem.* 256, 2258 (1981). In tests utilizing the above described procedure, the DBH inhibitory activity of the test compound increased as a function of the time of incubation as indicated in Table I:

TABLE I

| DBH INHIBITORY ACTIVITY - IN VITRO | | |
|---|---|---|
| Compound | Concentration | t ½* |
| β-ethenylidene 2-thiopheneethanamine | 1 mM | 78.2 min +/−1.1 |

*t ½ = time required for 50% inhibition.

The ability of compounds of this invention to lower blood pressure can be determined in vivo using hypertensive rats according to standard and well known procedures. The test compound is administered intraperitoneally (ip) to conscious rats and the blood pressure monitored continuously. Decreased mean blood pressure over time was observed when a compound of this invention was tested by the above described procedure, as indicated in Table II.

TABLE II

| ANTIHYPERTENSIVE ACTIVITY - IN VIVO | | | |
|---|---|---|---|
| Compound | Dose | Maximum % Change in mean Blood Pressure | Duration |
| β-ethenylidene-2-thiopheneethanamine | 50 mg/kg (ip) | 15.6 | 10 hr. |

Thus, based upon this and other standard laboratory techniques known to evaluate DBH inhibitors, by standard toxicity tests and by standard pharmacological assays for the determination of antihypertensive activity in mammals, and by comparison of these results with known antihypertensive agents, the effective antihypertensive dosage of the compounds of this invention can readily be determined. In general, the effective antihypertensive results can be achieved at a dose of about 5 to about 100 mg per kilogram of body weight per day. Of course, the specific initial and continuing dosage regimen for each patient will vary according to the nature and severity of the hypertension as determined by the attending diagnostician.

In their function as therapeutically useful compounds, it is advantageous to administer the compounds to the host animal as a composition in admixture with a pharmaceutically acceptable carrier suitable for internal administration, said carrier constituting a major portion of the admixture. Such preparations will be apparent to those skilled in the art and may be in such forms as, for example, tablets, capsules and suppositories, or in liquid forms, such as, for example, elixers, emulsions, sprays and injectables. In the formulation of pharmaceutical preparations there can be employed such substances which do not react with active substances as, for example, water, gelatin, lactose, starches, magnesium sterate, talc, vegetable oils, benzyl alcohols, gums, polyalkylene glycols, petroleum jelly and the like. The active ingredient of such pharmaceutical preparations is preferably present in the preparation in such proportions by weight that the proportion by weight of the active ingredient to be administered lies between 0.1% and 50%.

We claim:

1. A compound of the formula

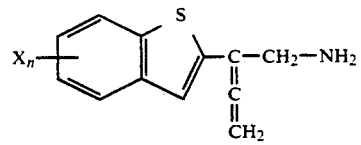

wherein n is the integer 0, 1 or 2; each X independently is a substituent selected from the group consisting of loweralkyl, halo, —O—(loweralkyl), —S—(loweralkyl), —SO—(loweralkyl), —SO$_2$—(loweralkyl), CO$_2$R and CH$_2$OR, wherein R is loweralkyl and each loweralkyl group is from 1 to about 6 carbon atoms, or a pharmaceutically acceptable addition salt thereof.

2. A compound of claim 1 wherein n is 0.
3. A compound of claim 1 wherein n is 1.
4. A compound of claim 3 wherein X is selected from the group consisting of halo and loweralkyl.
5. A compound of claim 3 wherein X is —O— or —S— (loweralkyl).
6. A compound of claim 3 wherein X is CO$_2$R.
7. The compounds of claim 3 wherein X is CH$_2$OR.

8. A compound of claim 3 wherein X is loweralkyl of from 1 to about 4 carbon atoms.

9. A process for preparing a compound of the formula

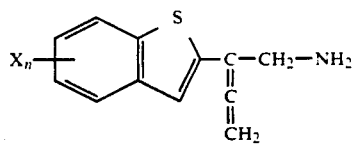

wherein n is the integer 0, 1 or 2; each X independently is a substituent selected from the group consisting of loweralkyl, halo, —O—(loweralkyl), —S—(loweralkyl), —SO—(loweralkyl), —SO$_2$—(loweralkyl), CO$_2$R and CH$_2$OR, wherein R is loweralkyl and each loweralkyl group is from 1 to about 6 carbon atoms, or a pharmaceutically acceptable addition salt thereof which comprises reacting a protected amine compound of the formula:

with a metallo-organic compound of the formula

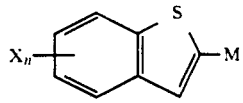

wherein X and n are as above defined, R' is alkoxy of from 1 to 4 carbon atoms, and M is an organometallo reagent, in the presence of an inert solvent and a nickel catalyst, and further treating the resulting product bearing a silyl protected amine group with a deprotecting agent to obtain the desired compound.

10. A pharmaceutical composition comprising a compound of claim 1, or a pharmaceutically acceptable addition salt thereof, in combination with a pharmaceutically acceptable carrier.

11. A method of treating hypertension in a mammal in need thereof which comprises administering to said mammal an antihypertensive effective amount of a compound of claim 1, or a pharmaceutically acceptable addition salt thereof.

* * * * *